(12) United States Patent
Sun et al.

(10) Patent No.: US 11,305,267 B2
(45) Date of Patent: Apr. 19, 2022

(54) CATALYST FOR PREPARING HIGH PURITY TAURINE AND USE THEREOF

(71) Applicant: HUBEI GRAND LIFE SCIENCE AND TECHNOLOGY CO., LTD, Hubei (CN)

(72) Inventors: Huajun Sun, Hubei (CN); Shangjin Yang, Hubei (CN); Ruyong Jiang, Hubei (CN); Chen Guo, Hubei (CN); Zhiqiang Qian, Hubei (CN)

(73) Assignee: HUBEI GRAND LIFE SCIENCE AND TECHNOLOGY CO., LTD, Hubei (CN)

( * ) Notice: Subject to any disclaimer, the term of this patent is extended or adjusted under 35 U.S.C. 154(b) by 0 days.

(21) Appl. No.: 17/369,963

(22) Filed: Jul. 8, 2021

(65) Prior Publication Data

US 2021/0331148 A1 Oct. 28, 2021

Related U.S. Application Data

(63) Continuation of application No. PCT/CN2019/106822, filed on Sep. 20, 2019.

(30) Foreign Application Priority Data

Jul. 1, 2019 (CN) .......................... 201910583398.9

(51) Int. Cl.
*B01J 31/02* (2006.01)
*C07C 303/22* (2006.01)
*C07C 303/32* (2006.01)

(52) U.S. Cl.
CPC ......... *B01J 31/0271* (2013.01); *C07C 303/22* (2013.01); *C07C 303/32* (2013.01)

(58) Field of Classification Search
None
See application file for complete search history.

(56) References Cited

U.S. PATENT DOCUMENTS 9,598,357 B1 * 3/2017 Hu .......................... B01J 31/04
2019/0135739 A1 * 5/2019 Hu .......................... C07C 303/32
2021/0179551 A1 * 6/2021 Hu .......................... C07C 303/02

FOREIGN PATENT DOCUMENTS

CN 1220702 A 6/1999
CN 1635911 A 7/2005
(Continued)

OTHER PUBLICATIONS

STNext, CAS Registry No. 857752-50-2, Aug. 1, 2005; Nosek et al., "Adrenolytic compounds. I. Derivatives of N-(2-chloroethyl)dibenzylamine", Chemicke Listy pro Vedu a Prumysl, 1952, vol. 46, p. 6732, only abstract of Nosek from STN.

*Primary Examiner* — Amy C Bonaparte

(57) ABSTRACT

Provided is a catalyst for preparing high-purity taurine, and the catalyst is N,N-disubstituted aminoethanesulfonic acid and has a structure represented by Formula I, in which $R^1$ and $R^2$ are each independently selected from alkyl, alkenyl, alkynyl, alkoxy, benzyl, sulfhydryl, thioether group, aryl, heteroaryl, amino, amide, imide, cyano, aldehyde group, carbonyl, carboxyl, sulfonic acid group, or ester group. Also provided is a method for preparing high-purity taurine, which adds the catalyst in an ammonolysis step for preparing taurine, thereby having effects of high yield, inhibition of impurity production and a reduced amount of ammonia used, etc. The catalyst has advantages of low cost, stable physical properties, and easy separation from the product. The preparation method is simple to operate with easily available raw materials and high yield, and can be employed for industrial production. Moreover, the purity of the prepared taurine can be up to 98% or higher.

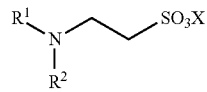

Formula I

18 Claims, 1 Drawing Sheet

(56) References Cited

FOREIGN PATENT DOCUMENTS

| CN | 101148427 | * | 3/2008 |
|---|---|---|---|
| CN | 101148427 A | | 3/2008 |
| CN | 106588710 A | | 4/2017 |
| CN | 108299263 A | | 7/2018 |
| CN | 109020839 A | | 12/2018 |

* cited by examiner

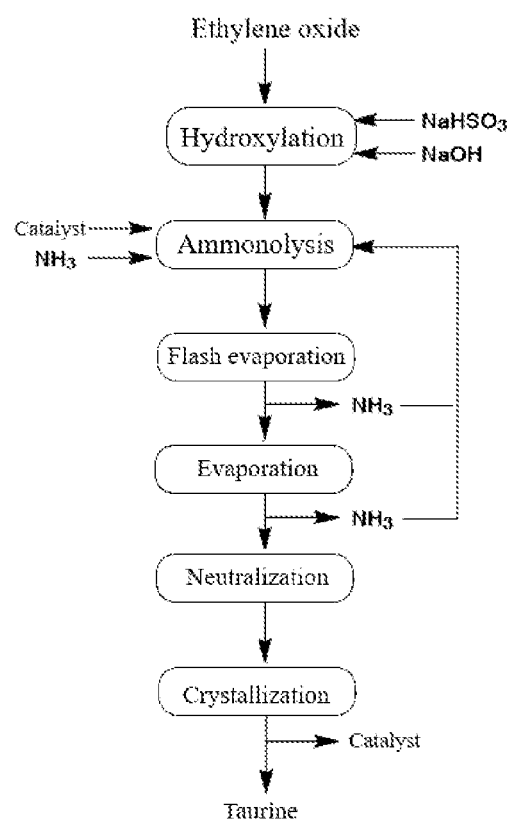

CATALYST FOR PREPARING HIGH PURITY TAURINE AND USE THEREOF

CROSS REFERENCE TO RELATED APPLICATIONS

This application is a continuation application of International Application No. PCT/CN2019/106822, filed on Sep. 20, 2019, which claims priority to Chinese Application No. 201910583398.9, filed on Jul. 1, 2019, the entire contents of which are incorporated herein by reference.

FIELD

The present disclosure relates to the technical field of catalysts, and particularly, relates to a catalyst for preparing taurine and use thereof.

BACKGROUND

Taurine, as a sulfamic acid, can be naturally produced by most mammals, and is an important nutrient for human and animals. Accordingly, taurine is often added to various foodstuffs, including infant formula milk powder, energy drinks, and pet foods.

In the past 30 years, around the world, taurine is typically obtained through chemical synthesis with an ethylene oxide-based taurine synthesis process, which was first reported in the 1930s (for example, DE612994C, DE593968C, U.S. Pat. Nos. 1,932,907 and 1,999,614).

Such a process includes the following reaction steps:
1. Hydroxylation Reaction

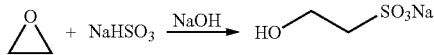

2. Ammonolysis Reaction

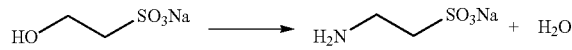

3. Neutralization Reaction

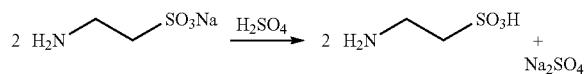

However, during the ammonolysis reaction of this process, sodium isethionate not only produces sodium taurinate, but also produces a small amount of by-product, sodium ditaurinate (DD26023). Moreover, sodium isethionate cannot be completely converted into sodium taurinate even under high temperature and high pressure environments, and the unreacted sodium isethionate still exists in the mother liquid of taurine in a free form.

SUMMARY

In order to solve the above technical problems, the present disclosure provides a catalyst for preparing high-purity taurine and a method for preparing high-purity taurine, which can significantly reduce the amount of ammonia used and increase the yield and purity of taurine, thereby significantly reducing the cost of preparation.

The catalyst according to the present disclosure is added in a step of ammonolysis for preparing taurine. The catalyst has a structure similar to sodium ditaurinate. In the ammonolysis reaction, addition of this catalyst can significantly increase the yield of ammonolysis, inhibit the generation of impurities, and reduce the amount of ammonia used. In addition, the catalyst provided by the present disclosure itself has advantages of low cost, easy availability, stable physical properties and easy separation from the product. The method for preparing taurine according to the present disclosure is simple to operate with easily available raw materials and high yield, and thus can be employed in industrial production. Moreover, the use of catalyst does not affect product quality, and the purity of the prepared taurine is up to 98% or higher.

Specifically, the catalyst provided by the present disclosure has a structure represented by Formula I:

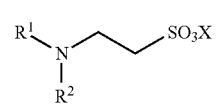

Formula I in which $R^1$ and $R^2$ are each independently selected from the group consisting of alkyl, alkenyl, alkynyl, alkoxy, benzyl, sulfhydryl, a thioether group, aryl, heteroaryl, amino, an amide group, an imide group, cyano, an aldehyde group, carbonyl, carboxyl, a sulfonic acid group, an ester group, and combinations thereof, wherein the above-mentioned carbon chain refers to a linear or branched C1-C40 chain;

preferably, the alkyl is a linear or branched saturated C1-C18 (preferably C1-C12, more preferably C1-C6) hydrocarbyl; particularly preferably, the alkyl is selected from methyl, ethyl, 1-propyl or n-propyl ("n-Pr"), 2-propyl or iso-propyl ("i-Pr"), 1-butyl or n-butyl ("n-Bu"), 2-methyl-1-propyl or iso-butyl ("i-Bu"), 1-methylpropyl or sec-butyl ("s-Bu"), 1,1-dimethylethyl or tert-butyl ("t-Bu");

the alkenyl is selected from linear or branched alkenyl groups containing at least one C=C double bond and 2 to 12 carbon atoms, preferably linear or branched alkenyl groups containing at least one C=C double bond and 2 to 8 carbon atoms, and more preferably vinyl, propenyl, or isopropenyl;

the alkynyl is selected from linear or branched alkynyl groups containing at least one C≡C triple bond and 2 to 12 carbon atoms, preferably linear or branched alkynyl groups containing at least one C≡C triple bond and 2 to 8 carbon atoms, and more preferably, ethynyl, propynyl, butynyl;

the alkoxy is linear or branched C1-C6 alkoxy, preferably methoxyl, ethoxyl, propoxyl, or isopropoxyl;

the thioether group is selected from a methyl sulfide group or an ethyl sulfide group;

the aryl is selected from phenyl or substituted phenyl, and the substituted phenyl means that at least one hydrogen on a benzene ring is substituted by a substituent selected from a hydrogen isotope, halogen, cyano, nitro, carboxyl, an ester group, unsubstituted methylthio, methylthio substituted with 1 to 3 fluorine atoms, C1-C8 alkyl, or C1-C8 alkoxy (one or more hydrogens in the alkyl or the alkoxy are optionally substituted by halogen); preferably, the substituted benzene ring is selected from 4-methylphenyl, 4-methoxyphenyl, 4-nitrophenyl, 4-fluorophenyl, 4-chlorophenyl, 4-(trifluoromethyl)phenyl, 4-bromophenyl, 3-fluorophenyl, 3-chlorophenyl, 4-(trifluoromethoxy)phenyl, 4-cyanophenyl, 2-fluorophenyl, 2-chlorophenyl, 2-(trifluoromethoxy)phenyl, 3,5-difluorophenyl, 3,5-dichlorophenyl, 2,4-difluorophenyl, 2,4-dichlorophenyl, 2,5-dichlorophenyl, 2,5-difluorophenyl, 3-chloro-4-fluorophenyl, 3,4-difluorophenyl, 3-chloro-5-(trifluoromethyl)phenyl, or 3,4,5-trifluorophenyl;

the heteroaryl is selected from a five- to seven-membered monocyclic aromatic ring containing at least one heteroatom or an eight- to twelve-membered bicyclic aromatic ring containing at least one heteroatom, in which the at least one heteroatom is selected from N, O or S, and the rest are carbon; preferably, the heteroaryl is selected from pyrrolyl, thienyl, indolyl, or benzofuranyl;

the amide group is an amide group substituted with a linear or branched C1-C18 alkyl, preferably acetylamino;

the imide group is an imide group substituted with a linear or branched C1-C18 alkyl, preferably acetylimido;

the carbonyl is alkoxycarbonyl, preferably methoxycarbonyl, ethoxycarbonyl, propoxycarbonyl or butoxycarbonyl; and the ester group is selected from an ester group substituted with linear or branched C1-C18 alkyl, an aryl ester group, or a carboxylic ester group, preferably formyloxy, acetoxy, isopropyl acyloxy, n-propyl acyloxy, allyl acyloxy, cyclopropyl acyloxy, n-butyl acyloxy, isobutyl acyloxy, sec-butyl acyloxy, tert-butyl acyloxy, n-pentyl acyloxy, isopentyl acyloxy, n-hexyl acyloxy, or isohexyl acyloxy; the aryl ester group includes any one of phenyl acyloxy and tolyl acyloxy; and the carboxylic ester group is selected from ethoxycarbonyl, methoxycarbonyl, n-propoxycarbonyl, isopropoxycarbonyl, n-butoxycarbonyl, sec-butoxycarbonyl, or n-hexyloxycarbonyl.

X is selected from H, a metal element of group IA, or a metal element of group IIA. Preferably, the metal element of group IA is selected from lithium, sodium, or potassium; and the metal element of group IIA is selected from magnesium, calcium, or barium.

As a particularly preferred embodiment, the present disclosure provides the following four structures, as represented by Formula II to Formula V.

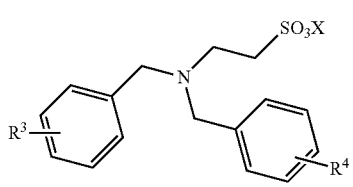

In the structure represented by Formula II, $R^3$ and $R^4$ are each independently selected from hydrogen, saturated or unsaturated C1-C20 hydrocarbyl, or saturated or unsaturated C1-C20 alkoxy; preferably, $R^3$ and $R^4$ are the same or different from each other, and are each independently selected from hydrogen or a saturated or unsaturated C1-C10 hydrocarbyl; and more preferably $R^3$ and $R^4$ are both hydrogen or methyl.

X is selected from H, a metal element of group IA, or a metal element of group IIA. Preferably, the metal element of group IA is selected from lithium, sodium, or potassium; and the metal element of group IIA is selected from magnesium, calcium, or barium.

Such catalysts have the advantages of good catalytic effect and easy separation.

The catalyst represented by Formula II is preferably

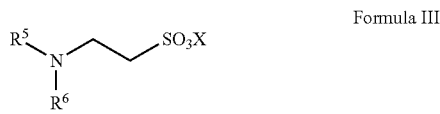

In Formula III, $R^5$ and $R^6$ are the same or different from each other, and are each independently selected from saturated or unsaturated C1-C18 hydrocarbyl; preferably, $R^5$ and $R^6$ are the same or different from each other, and are each independently selected from saturated or unsaturated C1-C12 hydrocarbyl, more preferably C8-C12 alkyl.

X is selected from H, a metal element of group IA, or a metal element of group IIA. Preferably, the metal element of group IA is selected from lithium, sodium, or potassium; and the metal element of group IIA is selected from magnesium, calcium, or barium.

Such catalysts have the advantages of good solubility and easy separation.

The catalyst represented by Formula III is preferably

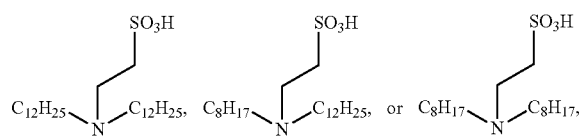

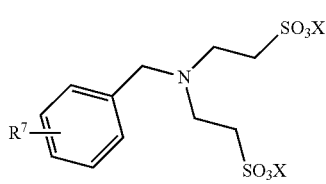

In Formula IV, $R^7$ is selected from hydrogen, saturated or unsaturated C1-C20 hydrocarbyl, or saturated or unsaturated C1-C20 alkoxy, preferably, $R^7$ is selected from hydrogen or saturated or unsaturated C1-C10 hydrocarbyl, and more preferably, $R^7$ is hydrogen or methyl; and X is selected from H, a metal element of group IA, or a metal element of group IIA. Preferably, the metal element of group IA is selected from lithium, sodium, or potassium; and the metal element of group IIA is selected from magnesium, calcium, or barium.

Such catalysts have the advantages of good catalytic effect, easy separation, and a high product yield.

The catalyst represented by Formula IV is preferably

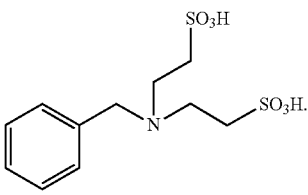 [SMILES: O=S(=O)(O)CCN(CCS(=O)(=O)O)Cc1ccccc1]

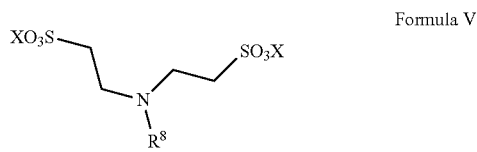

Formula V

In Formula V, $R^8$ is selected from hydrogen, or saturated or unsaturated C1-C18 hydrocarbyl; and X is selected from H, a metal element of group IA, or a metal element of group IIA, preferably H.

Preferably, $R^8$ is selected from saturated or unsaturated C1-C12 hydrocarbyl, more preferably methyl, ethyl or dodecyl. Such catalysts have the advantages of good solubility and good catalytic effect.

The catalyst represented by Formula V is preferably N-dodecylamino-N,N-bis (2-ethanesulfonic acid).

As the catalyst provided by the present disclosure, preferably, the salt is a sodium salt, more preferably sodium N,N-di(substituted benzyl)-2-aminoethanesulfonate, sodium N,N-dialkyl-2-aminoethanesulfonate, a sodium salt of N-(substituted benzyl)amino-N,N-bis(2-ethanesulfonic acid), or a sodium salt of N-alkylamino-N,N-bis(2-ethanesulfonic acid).

The present disclosure first proposes that the above-mentioned compound is used as a catalyst for preparing taurine. The provided catalyst has a structure of secondary amine, which is similar to sodium ditaurinate, such as N,N-di(substituted benzyl)-2-aminoethanesulfonic acid, N,N-disubstituted aminoethanesulfonic acid, N-(substituted benzyl)amino-N,N-bis(2-ethanesulfonic acid), N-alkylamino-N,N-bis(2-ethanesulfonic acid), etc. Based on the principle of chemical equilibrium, by inhibiting the formation of sodium ditaurinate in the ammonolysis reaction, the content of impurity sodium ditaurinate is reduced from source, and the chemical equilibrium reaction is shifted to the right, thereby increasing a conversion rate of sodium isethionate and increasing a yield of sodium taurinate.

Meanwhile, the present disclosure provides a method for preparing high-purity taurine, the method using the above-mentioned catalyst during ammonolysis.

After this catalyst is added, the content of the impurity sodium ditaurinate can be reduced from source, the conversion rate of sodium isethionate is increased, and the yield of sodium taurinate is enhanced.

Preferably, the method includes the following steps:
step S1, performing a hydroxylation reaction of ethylene oxide and sodium bisulfite to produce sodium isethionate;
step S2, performing ammonolysis of the sodium isethionate under the effect of the above-mentioned catalyst; and
step S3, neutralizing a product of the ammonolysis to obtain high-purity taurine.

In an embodiment of the present disclosure, the step S2 is specifically: mixing the sodium isethionate obtained in step S1 with ammonia, adding one or more of the catalysts of the present disclosure to obtain a reaction solution, performing an ammonolysis reaction at high temperature and high pressure, discharging a large amount of excess ammonia from the reaction solution through flash evaporation after the reaction is completed, then discharging the remaining ammonia and excess water through evaporation, and recycling the ammonia discharged through the flash evaporation and the evaporation as a raw material for the ammonolysis reaction.

In an embodiment of the present disclosure, the step S3 is specifically: acidifying a reaction solution obtained after the evaporation in the step S2 through direct acidification, ion exchange or electroosmosis/electroosmosis to replace sodium ions in molecules of sodium taurinate with hydrogen ions.

Through crystallization or other manners, the taurine is separated from the unreacted sodium isethionate and the catalyst by solid-liquid separation, so as to obtain a solid product of taurine.

The above-mentioned process flow for preparing high-purity taurine is shown in the FIGURE.

It was found in experiments that, upon analysis and test of the finally obtained reaction solution according to the method provided by the present disclosure, the solution contained sodium taurinate, a small amount of unreacted sodium isethionate and catalyst, but did not contain any by-product sodium ditaurinate.

In the method for preparing taurine according to the present disclosure, the sodium isethionate, as a raw material, is commercially available, or can be prepared by conventional methods known in the related art, for example, by reacting ethylene oxide with sodium bisulfite, which is not specifically limited in the present disclosure.

Preferably, a molar ratio of the catalyst to the sodium isethionate ranges from 0.1% to 15%, more preferably from 5% to 10%. Such an amount can bring advantages of good catalytic effect and complete inhibition of the formation of impurities.

Preferably, a molar ratio of the ammonia to the sodium isethionate ranges from 0.1:1 to 50:1, preferably from 6:1 to 8:1 (8:1 is especially preferred). At this molar ratio, the yield and quality of taurine can be advantageously improved.

Preferably, the ammonia is provided in a form of ammonia water at a concentration ranging from 20% to 35%, preferably from 25% to 35%, based on a total mass of the ammonia water.

Preferably, the ammonolysis reaction continues for 0.1 h to 40 h, preferably 1.5 h to 2 h.

Preferably, an acid used in the direct acidification includes organic acids, inorganic acids, various acidic gases, and acidic polymer compounds.

Preferably, the acidifying through ion exchange includes cation exchange, anion exchange, and combined anion and cation exchange. The acidifying through electrolysis/electroosmotic includes direct electrolysis, electrodialysis, and bipolar membrane electrodialysis.

Preferably, the method of the present disclosure further includes a step of recovering excess ammonia, that is, recovering the ammonia in the flash evaporation and evaporation steps for ammonolysis reaction of a next batch. The recovering can be carried out by conventional methods known in the related art, which is not specifically limited in the present disclosure.

Preferably, the method of the present disclosure further includes a step of separating the taurine from the unreacted sodium isethionate and the catalyst. The separating can be carried out by conventional methods known in the related art, which is not specifically limited in the present disclosure.

The method for preparing taurine according to the present disclosure is simple to operate with easily available raw materials and high yield, and thus can be used for industrial production, and the purity of the prepared taurine can be up to 98% or higher.

BRIEF DESCRIPTION OF DRAWINGS

The FIGURE is a flow diagram of a process for preparing taurine.

DESCRIPTION OF EMBODIMENTS

The following examples are for the purpose of illustrating the present disclosure, rather than limiting the scope of the present disclosure.

Example 1: Preparation of catalyst N,N-dibenzylamino-2-ethanesulfonic acid

This example provides a catalyst (N,N-dibenzylamino-2-ethanesulfonic acid) for preparing taurine, and the catalyst is obtained through the following method.

Taurine (0.5 mol, 62.58 g), sodium hydroxide (0.125 mol, 5 g), and benzyl alcohol (3 mol, 324.18 g) were sealed in an autoclave (1 L), heated to 220° C. to react for 2 hours, and then cooled naturally for 3 hours or more; the reaction solution was neutralized with concentrated sulfuric acid and then acidified to neutrality, to precipitate N,N-dibenzylamino-2-ethanesulfonic acid, which was filtered and dried, with a yield of 80%. $^1$H NMR (DMSO-$d_6$) δ: 2.01 (brs, 1H), 2.92 (m, 2H), 3.51 (m, 2H), 3.62 (m, 4H), 7.06-7.14 (m, 10H) ppm.

The reaction equation is as below:

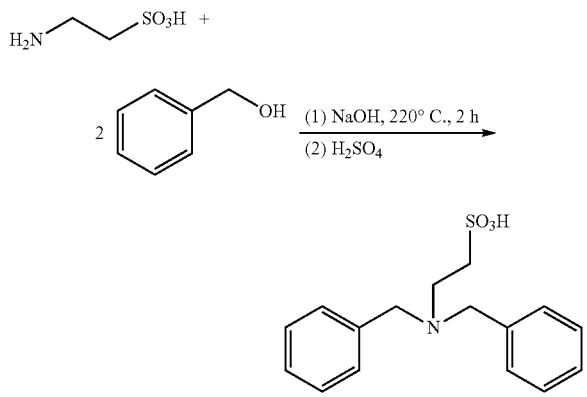

Example 2: Preparation of catalyst N-benzylamino-N,N-bis(2-ethanesulfonic acid)

This example provides a catalyst (N-benzylamino-N,N-bis(2-ethanesulfonic acid)) for preparing taurine, and the catalyst is obtained through the following method.

Benzylamine (0.5 mol, 53.58 mg), sodium hydroxide (0.125 mol, 5 g), and sodium isethionate (3 mol, 444.33 mg) were sealed in an autoclave (1 L), heated to 220° C. to react for 2 hours, and then cooled naturally for 3 hours or more; the reaction solution was neutralized with concentrated sulfuric acid and then acidified to pH 2-3, to precipitate N-benzylamino-N,N-bis(2-ethanesulfonic acid), which was filtered and dried, with a yield of 80%. $^1$H NMR (DMSO-$d_6$) δ: 2.0 (brs, 2H), 2.92 (m, 4H), 3.35 (m, 4H), 3.62 (m, 2H), 7.06-7.14 (m, 5H).

The reaction equation is as below:

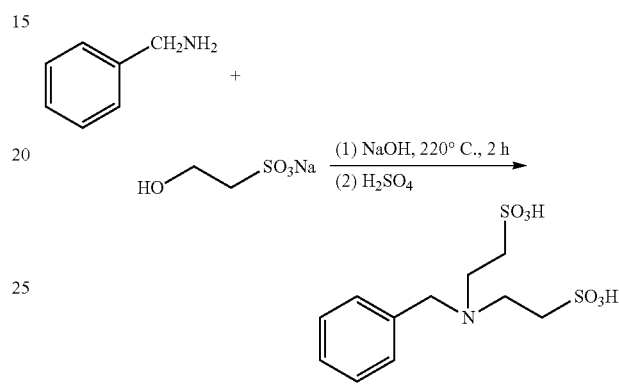

Example 3: Results of Ammonolysis Reaction at Different Times Using N,N-didodecyl-2-Aminoethanesulfonic Acid as a Catalyst This experimental example investigated the influence of the addition of N,N-didodecyl-2-aminoethanesulfonic acid as a catalyst on the ammonolysis reaction at different times. The experimental example was specifically performed as below. Sodium isethionate (0.5 mol, 74.06 g) was dissolved in 200 ml of 30% ammonia water, sodium hydroxide (0.125 mol, 5 g) and N,N-didodecyl-2-aminoethanesulfonic acid (0.05 mol, 23.09 g) were added, and the mixture was sealed in an autoclave (1 L) and heated to 220° C. After reacting for different times, cold water was introduced to terminate the reaction, and the reaction solution was directly analyzed to determine the contents of respective components. The results are shown in Table 1.

The reaction equation is as below:

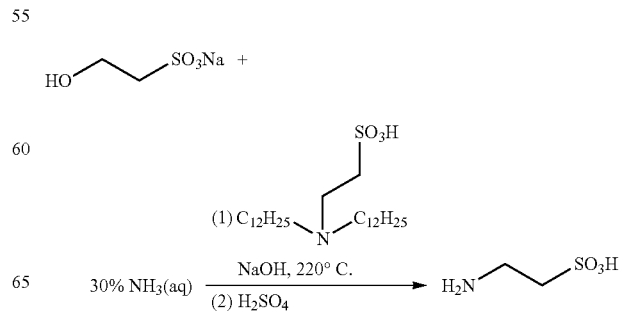

TABLE 1

Influence of reaction time on the product of ammonolysis after the addition of N,N-didodecyl-2-aminoethanesulfonic acid as a catalyst (a molar ratio of ammonia to sodium isethionate was 8)

| No. | Reaction time (min) | Percentages of substances in product | | |
|---|---|---|---|---|
| | | Sodium isethionate | Sodium taurinate | Sodium ditaurinate |
| 1 | 0 | 100 | 0 | 0 |
| 2 | 30 | 63 | 47 | 0 |
| 3 | 60 | 42 | 58 | 0 |
| 4 | 90 | 9 | 91 | 0 |
| 5 | 120 | 5 | 95 | 0 |
| 6 | 150 | 4 | 95 | 1 |

Example 4: Results at Different Amounts of Ammonia when Using N,N-didodecyl-2-aminoethanesulfonic acid as a Catalyst This experimental example investigates the influence of different amounts of ammonia used on the ammonolysis reaction after the addition of N,N-didodecyl-2-aminoethanesulfonic acid as the catalyst. The experimental example was specifically performed as below. Sodium isethionate (0.5 mol, 74.06 g) was dissolved in different amounts of 3000 ammonia water, sodium hydroxide (0.125 mol, 5 g) and N,N-didodecyl-2-aminoethanesulfonic acid (0.05 mol, 23.09 g) were added, and the mixture was sealed in an autoclave (1 L) and heated to 220° C. After reacting for 2 hours, cold water was introduced to terminate the reaction, and the reaction solution was directly analyzed to determine the contents of respective components. The results are shown in Table 2.

TABLE 2

Influence of the amount of ammonia used on the product of ammonolysis after the addition of N,N-didodecyl-2-aminoethanesulfonic acid as a catalyst (reaction time was 2 hours)

| No. | Ammonia/sodium isethionate (molar ratio) | Percentages of substances in product | | |
|---|---|---|---|---|
| | | Sodium isethionate | Sodium taurinate | Sodium ditaurinate |
| 7 | 0.1 | 73 | 2 | 5 |
| 8 | 0.5 | 49 | 38 | 9 |
| 9 | 1 | 37 | 53 | 7 |
| 10 | 5 | 10 | 87 | 2 |
| 11 | 8 | 5 | 95 | 0 |
| 12 | 10 | 2 | 98 | 0 |
| 13 | 15 | 1 | 99 | 0 |
| 14 | 20 | 0 | 100 | 0 |

Example 5: Results of the Ammonolysis Reaction at Different Reaction Times when Using N,N-dibenzyl-2-aminoethanesulfonic acid as a Catalyst This experimental example investigated the influence of the addition of N,N-dibenzyl-2-aminoethanesulfonic acid as the catalyst on the ammonolysis reaction at different times. The experimental example was specifically performed as below. Sodium isethionate (0.5 mol, 74.06 g) was dissolved in 200 ml of 30% ammonia water, sodium hydroxide (0.125 mol, 5 g) and N,N-dibenzyl-2-aminoethanesulfonic acid (0.05 mol, 15.26 g) were added, and the mixture was sealed in an autoclave (1 L) and heated to 220° C. After reacting for different times, cold water was introduced to terminate the reaction, and the reaction solution was directly analyzed to determine the contents of respective components. The results are shown in Table 3.

TABLE 3

Influence of a change of the reaction time on the product
of ammonolysis after the addition of
N,N-dibenzyl-2-aminoethanesulfonic acid as a catalyst
(a molar ratio of ammonia to sodium isethionate was 8)

| | | Percentages of substances in reaction solution | | |
|---|---|---|---|---|
| No. | Reaction time (mm) | Sodium isethionate | Sodium taurinate | Sodium ditaurinate |
| 1 | 0 | 100 | 0 | 0 |
| 2 | 30 | 57 | 43 | 0 |
| 3 | 60 | 46 | 54 | 0 |
| 4 | 90 | 9 | 91 | 0 |
| 5 | 120 | 2 | 98 | 0 |
| 6 | 150 | 0 | 98 | 2 |

Example 6: Results of the Ammonolysis Reaction with Different Proportions of Ammonia when Using N,N-Dibenzyl-2-Aminoethanesulfonic Acid as a Catalyst This experimental example investigated the influence of different molar ratios of ammonia to sodium isethionate on the ammonolysis reaction after the addition of N,N-dibenzyl-2-aminoethanesulfonic acid as the catalyst. The experimental example was specifically performed as below. Sodium isethionate (0.5 mol, 74.06 g) was dissolved in different amounts of 30% ammonia water, sodium hydroxide (0.125 mol, 5 g) and N,N-dibenzyl-2-aminoethanesulfonic acid (0.05 mol, 15.26 g) were added, and the mixture was sealed in an autoclave (1 L) and heated to 220° C. After reacting for 2 hours, cold water was introduced to terminate the reaction, and the reaction solution was directly analyzed to determine the contents of the various components. The results are shown in Table 4.

TABLE 4

Influence of a change of the molar ratio of ammonia to sodium
isethionate on the product of ammonolysis after the addition of
N,N-dibenzyl-2-aminoethanesulfonic acid
as a catalyst (reaction time was 2 hours)

| | Ammonia/sodium | Percentages of substances in reaction solution | | |
|---|---|---|---|---|
| No. | isethionate (molar ratio) | Sodium isethionate | Sodium taurinate | Sodium ditaurinate |
| 1 | 0.1 | 73 | 5 | 2 |
| 2 | 0.5 | 47 | 38 | 11 |
| 3 | 1 | 35 | 53 | 12 |
| 4 | 5 | 10 | 87 | 3 |
| 5 | 8 | 2 | 98 | 0 |
| 6 | 10 | 1 | 99 | 0 |
| 7 | 15 | 0 | 100 | 0 |
| 8 | 20 | 0 | 100 | 0 |

In connection with the data in Table 3 and Table 4, it can be known that when N,N-dibenzyl-2-aminoethanesulfonic acid is used as the catalyst, the most suitable conditions for the ammonolysis reaction of industrial production are as follows: the molar ratio of ammonia to sodium isethionate is controlled to be 8, and the reaction time is 2 hours, so that the high-purity taurine can be obtained with the highest efficiency.

Example 7: Results of the Ammonolysis Reaction at Different Reaction Times when Using N-benzylamino-N,N-bis(2-ethanesulfonic acid) as a Catalyst This experimental example investigated the influence of the addition of N-benzylamino-N,N-bis(2-ethanesulfonic acid) as the catalyst on the ammonolysis reaction at different times. The experimental example was specifically performed as below. Sodium isethionate (0.5 mol, 74.06 g) was dissolved in 200 ml of 30% ammonia water, sodium hydroxide (0.125 mol, 5 g) and N-benzylamino-N,N-bis(2-ethanesulfonic acid) (0.05 mol, 16.18 g) were added, and the mixture was sealed in an autoclave (1 L) and heated to 220° C. After reacting for different times, cold water was introduced to terminate the reaction, and the reaction solution was directly analyzed to determine the contents of various components. The results are shown in Table 5.

TABLE 5

Influence of a change of the reaction time on the product of ammonolysis after the addition of N-benzylamino-N,N-bis(2-ethanesulfonic acid) as a catalyst

| No. | Reaction time (mm) | Percentages of substances in reaction solution | | |
|---|---|---|---|---|
| | | Sodium isethionate | Sodium taurinate | Sodium ditaurinate |
| 1 | 0 | 100 | 0 | 0 |
| 2 | 30 | 56 | 44 | 0 |
| 3 | 60 | 47 | 53 | 0 |
| 4 | 90 | 10 | 90 | 0 |
| 5 | 120 | 2 | 98 | 0 |
| 6 | 150 | 0 | 98 | 2 |

Example 8: Results of the Ammonolysis Reaction with Different Proportions of Ammonia when Using N-benzylamino-N,N-bis(2-ethanesulfonic acid) as a Catalyst This experimental example investigates the influence of different amounts of ammonia used on the ammonolysis reaction after the addition of N-benzylamino-N,N-bis(2-ethanesulfonic acid) as the catalyst. The experimental example was specifically performed as below. Sodium isethionate (0.5 mol, 74.06 g) was dissolved in different amounts of 30% ammonia water, sodium hydroxide (0.125 mol, 5 g) and N-benzylamino-N,N-bis(2-ethanesulfonic acid) (0.05 mol, 16.18 g) were added, and the mixture was sealed in an autoclave (1 L) and heated to 220° C. After reacting for 2 hours, cold water was introduced to terminate the reaction, and the reaction solution was directly analyzed to determine the contents of various components. The results are shown in Table 6.

TABLE 6

Influence of a change of the molar ratio of ammonia to sodium isethionate on the product of ammonolysis after the addition of N-benzylamino-N,N-bis(2-ethanesulfonic acid) as a catalyst (reaction time was 2 hours)

| No. | Ammonia/sodium isethionate (molar ratio) | Percentages of substances in reaction solution | | |
|---|---|---|---|---|
| | | Sodium isethionate | Sodium taurinate | Sodium ditaurinate |
| 1 | 0.1 | 73 | 2 | 5 |
| 2 | 0.5 | 47 | 38 | 15 |
| 3 | 1 | 35 | 53 | 12 |
| 4 | 5 | 10 | 87 | 3 |
| 5 | 8 | 2 | 98 | 0 |
| 6 | 10 | 1 | 99 | 0 |
| 7 | 15 | 0 | 100 | 0 |
| 8 | 20 | 0 | 100 | 0 |

Based on the above examples, it can be seen that a conversion rate of sodium isethionate can reach 98% when the reaction time is 2 hours and the molar ratio of ammonia to sodium isethionate was 8; and the conversion rate can be enhanced to 99% or higher when the proportion of ammonia was further increased. Accordingly, upon taking cost and efficiency into consideration, it is believed that the optimal reaction time is 2 hours, and the optimal molar ratio of ammonia to sodium isethionate is 8.

Example 9: Catalysis Results Under Optimal Conditions when Using N-methylamino-N,N-bis(2-ethanesulfonic acid) as a Catalyst Sodium isethionate (0.5 mol, 74.06 g) was dissolved in 200 ml of 30% ammonia water, sodium hydroxide (0.125 mol, 5 g) and N-methylamino-N,N-bis(2-ethanesulfonic acid) (0.05 mol, 12.35 g) were added, and the mixture was sealed in an autoclave (1 L) and heated to 220° C. After reacting for 2 h, cold water was introduced to terminate the reaction, and the excess ammonia was removed. The percentages of substances in the reaction system were detected, the content of sodium taurinate was 96%, and the content of sodium isethionate was 4%.

Example 10: Catalysis Results Under Optimal Conditions when Using Sodium N-Methyl Ditaurinate

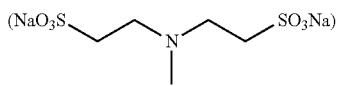

as a Catalyst

Sodium isethionate (0.5 mol, 74.06 g) was dissolved in 200 ml of 30% ammonia water, sodium hydroxide (0.125 mol, 5 g) and sodium N-methyl ditaurinate (0.05 mol, 14.55 g) were added, and the mixture was sealed in an autoclave (1 L) and heated to 220° C. After reacting for 2 h, cold water was introduced to terminate the reaction, and the excess ammonia was removed. The percentages of substances in the reaction system were detected, the content of sodium taurinate was 95%, and the content of sodium isethionate was 5%.

Although the present disclosure is described in detail with the above generic description and specific examples, modifications and improvements that are apparent to those skilled in the art that can be made based on the present disclosure. Thus, these modifications and improvements made without departing from the spirit of the present disclosure shall fall within the protection scope of the present disclosure.

INDUSTRIAL APPLICABILITY

The present disclosure provides a catalyst for preparing high-purity taurine, and the catalyst is N,N-disubstituted aminoethanesulfonic acid and has a structure represented by Formula I. In the Formula I, $R^1$ and $R^2$ are each independently selected from alkyl, alkenyl, alkynyl, alkoxy, benzyl, sulfhydryl, a thioether group, aryl, substituted aryl, heteroaryl, substituted heteroaryl, amino, an amide group, an imide group, cyano, an aldehyde group, carbonyl, carboxyl, a sulfonic acid group, a substituted sulfonic acid group, or an ester group. The present disclosure also provides a method for preparing high-purity taurine, which adds the catalyst according to the present disclosure in an ammonolysis step for preparing the taurine, thereby having the effects of high yield, inhibition of impurity production and a reduced amount of ammonia used, etc. The catalyst has the advantages of low cost, stable physical properties, and easy separation from the product. The preparation method according to the present disclosure is simple to operate with easily available raw materials and high yield, and thus can be employed for industrial production. Moreover, the purity of the prepared taurine can be up to 98% or higher, thereby providing better economic value and application prospects.

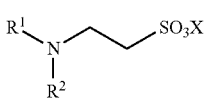

Formula I

The invention claimed is:

1. A method for preparing taurine, comprising using a catalyst having a structure represented by Formula I in an ammonolysis process of the method,

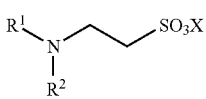

Formula I wherein $R^1$ and $R^2$ are each independently selected from the group consisting of alkyl, alkenyl, alkynyl, alkoxy, sulfhydryl, a thioether group, aryl, heteroaryl, amino, an amide group, an imide group, cyano, an aldehyde group, carbonyl, carboxyl, a sulfonic acid group, an ester group, and combinations thereof; and X is selected from H, a metal element of group IA, or a metal element of group IIA;

the alkyl is a linear or branched saturated C1-C18 hydrocarbyl;

the alkenyl is selected from linear or branched alkenyl groups containing at least one C=C double bond and 2 to 12 carbon atoms;

the alkynyl is selected from linear or branched alkynyl groups containing at least one C≡C triple bond and 2 to 12 carbon atoms;

the alkoxy is selected from linear or branched C1-C6 alkoxy;

the thioether group is selected from a methyl sulfide group or an ethyl sulfide group;

the aryl is selected from phenyl or substituted phenyl, wherein the substituted phenyl means that at least one hydrogen on a benzene ring is substituted by a substituent selected from a hydrogen isotope, halogen, cyano, nitro, carboxyl, an ester group, unsubstituted methylthio, methylthio substituted with 1 to 3 fluorine atoms, C1-C8 alkyl, or C1-C8 alkoxy;

the heteroaryl is selected from a five- to seven-membered monocyclic aromatic ring containing at least one heteroatom or an eight- to twelve-membered bicyclic aromatic ring containing at least one heteroatom, wherein the at least one heteroatom is selected from N, O or S, and the rest are carbon;

the amide group is an amide group substituted with a linear or branched C1-C18 alkyl;

the imide group is an imide group substituted with a linear or branched C1-C18 alkyl;

the carbonyl is alkoxycarbonyl; and the ester group is selected from an ester group substituted with a linear or branched C1-C18 alkyl, an aryl ester group, or a carboxylic ester group.

2. The method according to claim 1, comprising:

step S1 of performing a hydroxylation reaction of ethylene oxide and sodium bisulfite to produce sodium isethionate;

step S2 of performing ammonolysis of the sodium isethionate under effect of one or more catalysts represented by Formula I; and step S3 of neutralizing a product of the ammonolysis to obtain the taurine.

3. The method according to claim 2, comprising:

step S1 of reacting ethylene oxide with a sodium bisulfite solution to produce sodium isethionate;

step S2 of mixing the sodium isethionate obtained in step S1 with ammonia, adding the one or more catalysts to obtain a reaction solution, performing an ammonolysis reaction at high temperature and high pressure, discharging excess ammonia from the reaction solution through flash evaporation after the ammonolysis reaction is completed, then discharging the remaining ammonia and excess water through evaporation, and recycling the ammonia discharged through the flash evaporation and the evaporation as a raw material for the ammonolysis reaction;

step S3 of acidifying a reaction solution obtained after the evaporation in step S2 through direct acidification, ion exchange or electrolysis/electroosmosis to replace sodium ions in molecules of sodium taurinate with hydrogen ions; and separating the taurine from the unreacted sodium isethionate and the one or more catalysts through solid-liquid separation to obtain a solid product of the taurine.

4. The method according to claim 2, wherein a molar ratio of the one or more catalysts to the sodium isethionate ranges from 0.1% to 15%.

5. The method according to claim 3, wherein a molar ratio of the one or more catalysts to the sodium isethionate ranges from 0.1% to 15%.

6. The method according to claim 2, wherein a molar ratio of the ammonia to the sodium isethionate ranges from 0.1:1 to 50:1; and/or
the ammonia is provided in a form of ammonia water at a concentration ranging from 20% to 35%, based on a total mass of the ammonia water; and/or
the ammonolysis reaction continues for 0.1 h to 40 h.

7. The method according to claim 3, wherein a molar ratio of the ammonia to the sodium isethionate ranges from 0.1:1 to 50:1; and/or
the ammonia is provided in a form of ammonia water at a concentration ranging from 20% to 35%, based on a total mass of the ammonia water; and/or
the ammonolysis reaction continues for 0.1 h to 40 h.

8. The method according to claim 6, wherein a molar ratio of the ammonia to the sodium isethionate ranges from 6:1 to 8:1; and/or
the ammonia is provided in a form of ammonia water at a concentration ranging from 25% to 35%, based on a total mass of the ammonia water; and/or
the ammonolysis reaction continues for 1.5 h to 2 h.

9. The method according to claim 7, wherein a molar ratio of the ammonia to the sodium isethionate ranges from 6:1 to 8:1; and/or
the ammonia is provided in a form of ammonia water at a concentration ranging from 25% to 35%, based on a total mass of the ammonia water; and/or
the ammonolysis reaction continues for 1.5 h to 2 h.

10. The method according to claim 3, wherein an acid used in the direct acidification comprises organic acids, inorganic acids, acidic gases, and acidic polymer compounds;
the acidifying through ion exchange comprises cation exchange, anion exchange, and combined anion and cation exchange; and
the acidifying through the electrolysis/electroosmotic comprises direct electrolysis, electrodialysis, and bipolar membrane electrodialysis.

11. The method according to claim 1, wherein
the alkenyl is selected from linear or branched alkenyl groups containing at least one C=C double bond and 2 to 8 carbon atoms;
the alkynyl is selected from linear or branched alkynyl groups containing at least one C≡C triple bond and 2 to 8 carbon atoms;
the alkoxy is selected from methoxy, ethoxy, propoxy, or isopropoxy;
the heteroaryl is selected from pyrrolyl, thienyl, indolyl, or benzofuranyl;
the amide group is acetylamino;
the imide group is acetylimido; and
the carbonyl is selected from methoxycarbonyl, ethoxycarbonyl, propoxycarbonyl or butoxycarbonyl.

12. The method according to claim 11, wherein
the alkyl is a linear or branched saturated C1-C6 hydrocarbyl;
the alkenyl is selected from vinyl, propenyl, or isopropenyl; and
the alkynyl is selected from ethynyl, propynyl, or butynyl.

13. A method for preparing taurine, comprising using a catalyst having a structure represented by any one of Formula II to Formula V in an ammonolysis process of the method,

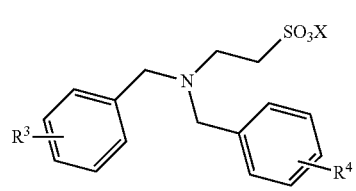

Formula II wherein in the structure represented by Formula II, $R^3$ and $R^4$ are each independently selected from saturated or unsaturated C1-C20 hydrocarbyl, or saturated or unsaturated C1-C20 alkoxy; and X is selected from H, a metal element of group IA, or a metal element of group IIA;

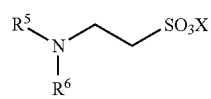

Formula III wherein $R^5$ and $R^6$ are the same or different from each other, and are each independently selected from saturated or unsaturated C1-C18 hydrocarbyl; and X is selected from H, a metal element of group IA, or a metal element of group IIA;

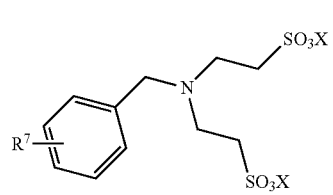

Formula IV wherein $R^7$ is selected from hydrogen, saturated or unsaturated C1-C20 hydrocarbyl, or saturated or unsaturated C1-C20 alkoxy; and X is selected from H, a metal element of group IA, or a metal element of group IIA;

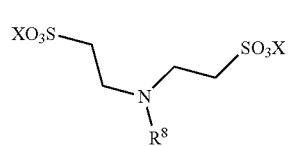

Formula V wherein $R^8$ is selected from hydrogen, or saturated or unsaturated C1-C18 hydrocarbyl; and X is selected from H, a metal element of group IA, or a metal element of group IIA.

14. The method according to claim 13, wherein in the structure represented by Formula II, $R^3$ and $R^4$ are the same or different from each other, and are each independently selected from saturated or unsaturated C1-C10 hydrocarbyl;

in the structure represented by Formula III, $R^5$ and $R^6$ are the same or different from each other, and are each independently C1-C12 alkyl;

in the structure represented by Formula IV, $R^7$ is selected from hydrogen or saturated or unsaturated C1-C10 hydrocarbyl; and in the structure represented by Formula V, $R^8$ is selected from saturated or unsaturated C1-C12 hydrocarbyl and X is H.

15. The method according to claim 14, wherein $R^5$ and $R^6$ are the same or different from each other, and are each independently C8-C12 alkyl;

$R^7$ is hydrogen or methyl; and $R^8$ is methyl, ethyl or dodecyl.

16. The method according to claim 13, wherein X is sodium.

17. The method according to claim 16, wherein the catalyst has a structure represented by any one of Formula III, Formula IV, or Formula V, wherein X is sodium.

18. The method according to claim 13, wherein the catalyst is any one selected from the following structures:

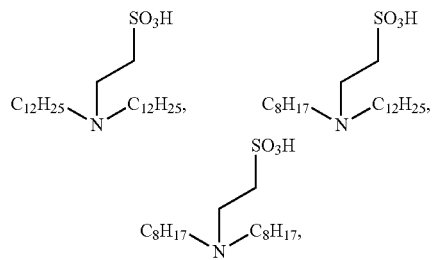

or N-dodecylamino-N,N-bis(2-ethanesulfonic acid).